United States Patent [19]

Reusser et al.

[11] Patent Number: 4,749,568

[45] Date of Patent: Jun. 7, 1988

[54] RUBRADIRIN TREATMENT OF METHICILLIN-RESISTANT STAPH

[75] Inventors: Fritz Reusser, Portage; Gary E. Zurenko; John H. Coats, both of Kalamazoo, all of Mich.

[73] Assignee: The Upjohn Company, Kalamazoo, Mich.

[21] Appl. No.: 6,394

[22] Filed: Jan. 23, 1987

[51] Int. Cl.$^4$ .............................................. A61K 35/74
[52] U.S. Cl. .................................... 424/119; 424/404; 424/414; 435/128; 435/886

[58] Field of Search ...................... 424/119, 404, 414; 435/128, 886

[56] References Cited

U.S. PATENT DOCUMENTS 3,335,057 8/1967 Johnson et al. ...................... 424/119
4,137,410 1/1979 Hoeksema ....................... 424/119 X Primary Examiner—Howard E. Schain
Attorney, Agent, or Firm—Bruce Stein

[57] ABSTRACT

It has been discovered that rubradirin can be used to treat rubradirin-sensitive, methicillin-resistant staphylococcal infections.

18 Claims, No Drawings

RUBRADIRIN TREATMENT OF METHICILLIN-RESISTANT STAPH

BACKGROUND OF THE INVENTION

1. Field of the Invention

This invention involves the use of the antibiotic rubradirin to treat methicillin-resistant (multiply antibiotic resistant) staphylococcal infections in humans and useful domesticated animals.

2. Description of the Related Art

Rubradirin is known, see U.S. Pat. No. 3,335,057.

U.S. Pat. No. 3,335,057 disclosed that rubradirin was useful in treating gram-positive infections including those of Staphylococcus aureus (S. aureus).

Bhuyan et al, in Antimicrobial Agents and Chemotherapy 91 (1964), disclosed that rubradirin had in vitro activity against two clinical strains of S. aureus which were resistant to several antibiotics. However, at that time, resistant S. aureus was not regarded as a clinically significant problem because clinical strains of S. aureus were sensitive to a number of antibiotics including methicillin and could be treated with methicillin. However, the strains originally tested by Bhuyan et al, in a latter study were found to be methicillin sensitive. Now, however, infectious stapylococci have become resistant to many antibiotics including methicillin. This is regarded not only as a theoretical problem but a very real one for the physician. These gram-positive bacteria are commonly referred to as methicillin-resistant S. aureus (MRSA) and methicillin-resistant S. epidermidis (MRSE). In practice, MRSA and MRSE are not only resistant to methicillin, but rather are resistant to multiple antibiotics including all penicillins and cephalosporins. Individual isolates are often resistant to lincosamides, macrolides, aminoglycosides and chloramphenicol. Thus, the laboratory finding that an isolate is methicillin-resistant usually indicates clinical resistance to multiple antibiotics. Multidrug-resistant staphylococci have retained their susceptibility to vancomycin, see Orthopedic Clinics of North America 15, 417 (1984).

Methicillin is a $\beta$-lactamase stable, semi-synthetic penicillin derivative and was developed to overcome staphylococcal resistance due to enzymatic inactivation. The drug was introduced in Europe in 1960, and methicillin-resistant strains were recognized soon thereafter, see Annals Intern. Med. 97, 440 (1982). Through the 1960's methicillin resistance appeared to be a rare, naturally-occurring phenomenon, of little clinical significance. Increasing isolation of MRSA became evident in the 1970's, as diverse strains emerged in many parts of the world, and produced serious clinical problems, see Annals Intern. Med. 97, 297 (1982). During this time, few reports of MRSA originated in the United States. However, in the late 1970's and early 1980's it became apparent that MRSA and MRSE were becoming important causes of hospital-acquired (i.e. nosocomial) infections, especially in burn units and intensive care wards. The organisms are of special significance since they frequently cause life-threatening disease, including pneumonia, bacteremia, and endocarditis. The number of effective therapeutic agents is extremely limited.

It has been discovered that rubradirin can successfully be used to treat rubradirin-sensitive, methicillin-resistant staphylococcal infections.

SUMMARY OF THE INVENTION

Disclosed is a method for the treatment of an animal infected with a rubradirin-sensitive, methicillin-resistant Staphylococcus which comprises administering an effective amount of rubradirin, or salt thereof, to the infected animal.

DETAILED DESCRIPTION OF THE INVENTION

The production, extraction and purification of rubradirin is known, see U.S. Pat. 3,335,057.

Rubradirin is used and administered either as the free acid or pharmaceutically acceptable salt. Examples of pharmaceutically acceptable salts include sodium, potassium, and calcium.

It is known to those skilled in the art how to formulate rubradirin, or a pharmaceutically acceptable salt, into the appropriate pharamaceutical dosage forms for oral (tablet, capsule), parenteral (sterile solution) or topical (creams, ointments or lotion) use.

Rubradirin is useful in treating rubradirin-sensitive, methicillin-resistant Staphylococcus infections in humans and useful domesticated animals. The staphylococcal infections are usually either S. aureus or S. epidermidis. It is preferred that the animal be a human. Other useful warm-blooded animals which have rubradirin-sensitive, methicillin-resistant Staphylococcus infections are cattle, sheep, pigs, horses, chickens, dogs and cats.

When rubradirin is administered orally, it is administered from about 1 to about 20 mg/kg, from one to four times daily. Preferred is about 4 to about 15 mg/kg, one to four times daily. when rubradirin is administered parenterally it can be given in an injection or IV infusion. When administered parenterally rubradirin is given in the same amount as when given orally, from about 1 to 80 mg/kg/day, preferably from about 4 to 60 mg/kg/day using the appropriate volumes and concentrations to effectuate these dosages. When administered IV, rubradirin, is infused in the usual manner at a rate of about 60 ml/hr to about 120 ml/hr, depending on the concentration of the rubradirin solution and the total amount of rubradirin to be given to the patient.

In treating topical infections, rubradirin is applied topically to the affected areas as is known in the art in the form of an ointment, cream or lotion.

Rubradirin can be either used alone or used with other antibiotics as is known to those skilled in the art.

It is known to those skilled in the art how to determine which Staphylococcus (aureus or epidermidis) infections are rubradirin-sensitive and methicillin-resistant by use of standarad susceptibility tests. See, "Dilution Susceptibility Test: agar and macro-broth dilution procedures; Manual of Clinical Microbiology, Third Edition, American Society of Microbiology, 1980, Washington, D.C., p 453–458".

The exact route of administration, dose, frequency of administration, use of other antibiotics or other pharmaceutical agents depends on the particular disease (particular microorganism), the severity of the disease, the age, general physical condition, weight, other clinical abnormalities etc of the particular patient to be treated as is known to those skilled in the art.

DEFINITIONS

The definitions and explanations below are for the terms as used throughout this entire document including both the specification and the claims.

MRSA refers to methicillin-resistant *S. aureus*.

MRSE referes to methicillin-resistant *S. epidermidis*.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

IV refers to intravenous.

EXAMPLES

Without further elaboration, it is believed that one skilled in the art can, using the preceding description, practice the present invention to its fullest extent. The following detailed examples described how to use rubradirin to treat rubradirin-sensitive, methicillin-resistant Staphylococcus infections in useful warm-blooded animals, in particular man and are to be construed as merely illustrative, and not limitations of the preceding disclosure in any way whatsoever. Those skilled in the art will promptly recognize appropriate variations from the examples because of variation in disease, the particular patient and condition to be treated.

EXAMPLE 1

A 70 kg male has a fever of 103° F. and has symptoms of bacterial pneumonia infection. Standard laboratory tests isolate an organism which is identified as *Staphylococcus aureus*. Susceptibility test results indicate that the isolate is resistant to methicillin and related antibiotics, but susceptible to rubradirin. The patient is given 1000 mg of rubradirin three times daily by mouth. The temperature over a short period goes to 98.6° F. and the clinical symptoms of pneumonia disappear.

EXAMPLE 2

A 60 kg female patient has an infection on her arm following a severe burn. She has a 101° F. fever. Standard laboratory tests isolate an organism which is identified as *Staphylococcus aureus*. Susceptibility test results indicate that the isolate is resistant to methicillin and related antibiotics, but susceptible to rubradirin. The patient is treated with a cream containing 3% rubradirin. The patients temperature after 3 days goes to normal, there is less inflammation, and the wound is not infected and appears to be healing much better.

EXAMPLE 3

A 85 kg male has baceterial endocarditis with a fever of 104° F. Standard laboratory tests isolate an organism which is identified as *Staphylococcus aureus*. Susceptibility test results indicate that the isolate is resistant to methcillin and related antibiotics, but susceptible to rubradirin. The patient is treated with an IV infusion of rubradirin (4.5 mg/ml) at a rate of 60 ml/hr for a dose of 76 mg/kg/day.

EXAMPLE 4

In Vivo Efficacy of Rubradirin

Effective Dose$_{50}$ (ED$_{50}$) determinations were performed using standard methods. All mice (Charles Fisher #1, 20 g) were given sufficient *S. aureus* intraperitoneally (IP) to kill 90 to 100% of untreated mice. At least five dosage levels of antibiotics were employed per each ED$_{50}$ determination. The antibiotic was administered subcutaneous (SQ) or orally at 1 and 5 hr post infection. The mice were monitored for one week with deaths being noted daily. The ED$_{50}$ values were calculated by probit analysis.

| Organism | ED$_{50}$ (mg/kg)[1] Rubradirin | | Control Antibiotic Paldimycin[2] |
|---|---|---|---|
| | SQ | Oral | |
| *S. aureus* UC6685 | 4.7 | 11.1 | 8.1 |
| *S. aureus* UC9213 | 4.7 | 1.6 | 12.7 |
| *S. aureus* UC9271 | 23.1 | 141 | 20.5 |

[1] The dose of drug in mg/kg of body weight required to protect 50% of the infected animals. Drug was dosed one and five hours post infection either orally or SQ.
[2] Paldimycin was dosed SQ.

We claim:

1. A method for the treatment of an animal infected with a rubradirin-sensitive, methicillin-resistant staphylococcus which comprises administering an effective amount of rubradirin, or salt thereof, to the infected animal.

2. A method according to claim 1 where the animal is a human.

3. A method according to claim 1 where the animal is a domesticated animal selected from the group consisting of cattle, sheep, pigs, horses, chickens, dogs and cats.

4. A method according to claim 1 where the staphylococcus is *S. aureus*.

5. A method according to claim 1 where the staphylococcus is *S. epidermidis*.

6. A method according to claim 1 where the route of administration is oral.

7. A method according to claim 6 where the effective amount is from about 1 to about 80 mg/kg/day.

8. A method according to claim 7 where the effective amount is from about 4 to about 60 mg/kg/day.

9. A method according to claim 1 where the route of administration is parenteral.

10. A method according to claim 9 where the administration is by injection.

11. A method according to claim 10 where the effective amount is from about 1 to about 80 mg/kg/day.

12. A method according to claim 11 where the effective amount is from about 4 to about 60 mg/kg/day.

13. A method according to claim 9 where the administration is by IV.

14. A method according to claim 13 where the effective amount is from about 1 to about 80 mg/kg/day.

15. A method according to claim 14 where the effective amount is from about 4 to about 60 mg/kg/day.

16. A method according to claim 1 where the treatment results in an improvement in clinical signs.

17. A method according to claim 1 where the rubradirin is in the free acid form.

18. A method according to claim 1 where the salt of rubradirin is the sodium, potassium or calcium form.

* * * * *